United States Patent
Swartz et al.

(10) Patent No.: US 7,338,789 B2
(45) Date of Patent: Mar. 4, 2008

(54) METHODS OF IN VITRO PROTEIN SYNTHESIS

(75) Inventors: James Robert Swartz, Stanford, CA (US); Michael Christopher Jewett, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/643,683

(22) Filed: Aug. 18, 2003

(65) Prior Publication Data

US 2004/0209321 A1   Oct. 21, 2004

Related U.S. Application Data

(60) Provisional application No. 60/404,591, filed on Aug. 19, 2002.

(51) Int. Cl.
*C12P 21/04* (2006.01)
*C12P 19/34* (2006.01)

(52) U.S. Cl. .................... 435/71.2; 435/91.3

(58) Field of Classification Search ............ 435/69.1
See application file for complete search history.

(56) References Cited

U.S. PATENT DOCUMENTS 5,478,730 A * 12/1995 Alakhov et al. ........... 435/68.1
6,337,191 B1    1/2002 Swartz et al.

OTHER PUBLICATIONS

Kim et al., J. Biotechnol. 84, 27-32, 2000.*
Baranov et al., Methods in Enzymology, 217, 123-142, 1993.*
Chen et al., Methods in Enzymology, vol. 101, 674-690, 1983.*
Dorner et la., Proc. Nat. Acad. Sci. USA, 76 (10):4832-4836, 1979.*
Raney et al., J. Biol. Chem., 275(32): 24444-24450, 2000.*
Yoshida et la., J. Blol. Chem. , 274 (32): 22723-22728, 1999.*
Kim et al., Prolonging Cell-Free Protein Synthesis by Selective Reagent Additions, Biotechnol. Prog., 2000, p. 385-390, vol. 16.
Kim et al., Expression—independent consumption of substrates in cell-free expression system from *Escherichia coli*, J. of Biotechnology, 2000, 84: 27-32.
Shimizu et al., Cell—free translation reconstituted with purified components, Nature Biotechnology, 2001, 19: 751-755.
Swartz J.R., "Advances in *Escherichia coli* production of therapeutic proteins." Current Opinion in Biotechnology, GB, vol. 12, No. 2, (Apr. 2001), pp. 195-201.

* cited by examiner

*Primary Examiner*—Nancy Vogel
(74) *Attorney, Agent, or Firm*—Bozicevic, Field & Francis LLP; Pamela J. Sherwood

(57) ABSTRACT

Biological macromolecules are synthesized in vitro under conditions and in a reaction composition wherein oxidative phosphorylation is activated and protein folding is improved.

10 Claims, 8 Drawing Sheets

METHODS OF IN VITRO PROTEIN SYNTHESIS

BACKGROUND OF THE INVENTION

Protein synthesis is a fundamental biological process that underlies the development of polypeptide therapeutics, diagnostics, and industrial enzymes. With the advent of recombinant DNA (rDNA) technology, it has become possible to harness the catalytic machinery of the cell to produce a desired protein. This can be achieved within the cellular environment or in vitro using extracts derived from cells.

Over the past decade, the productivity of cell-free systems has improved 2-orders of magnitude, from about 5 μg/ml-hr to about 500 μg/ml-hr. This accomplishment has made in vitro protein synthesis a practical technique for laboratory-scale research and provides a platform technology for high-throughput protein expression. It also begins to suggest the feasibility for using cell-free technologies as an alternative means to in vivo large-scale production of protein pharmaceuticals.

Cell-free protein synthesis offers several advantages over conventional, in vivo, protein expression methods. Cell-free systems can direct most, if not all, of the metabolic resources of the cell towards the exclusive production of one protein. Moreover, the lack of a cell wall and membrane components in vitro is advantageous since it allows for control of the synthesis environment. For example, tRNA levels can be changed to reflect the codon usage of genes being expressed. The redox potential, pH, or ionic strength can also be altered with greater flexibility than in vivo since we are not concerned about cell growth or viability. Furthermore, direct recovery of purified, properly folded protein products can be easily achieved.

In vitro translation is also recognized for its ability to incorporate unnatural and isotope-labeled amino acids as well as its capability to produce proteins that are unstable, insoluble, or cytotoxic in vivo. In addition, cell-free protein synthesis may play a role in revolutionizing protein engineering and proteomic screening technologies. The cell-free method bypasses the laborious processes required for cloning and transforming cells for the expression of new gene products in vivo, and is becoming a platform technology for this field.

Despite all of the promising features of cell-free protein synthesis, its practical use and large-scale implementation has been limited by several obstacles. Paramount among these are short reaction times and low protein production rates, which lead to poor yields of protein synthesis and excessive reagent cost. The pioneering work of Spirin et al. (1988) *Science* 242:1162-1164 initially circumvented the short reaction times problem with the development of a continuous flow system. Many laboratories have duplicated and improved upon this work, but they have all primarily used methods that constantly supply substrates to the reaction chamber. This approach increases the duration of the translation reaction and protein yield as compared to the batch system. However, it is inefficient in its use of expensive reagents, generally produces a dilute product, and has not provided significant improvements in production rates.

The conventional batch system offers several advantages over these continuous and semi-continuous schemes, which include ease of scale-up, reproducibility, increased protein production rates, convenience, applicability for multiplexed formats for high throughput expression, and more efficient substrate use. These advantages make improving the batch system productivity crucial for the industrial utilization of cell-free protein synthesis. Recently, a series of findings have been reported which begin to elucidate the causes of early termination of protein synthesis in batch reactions. Furthermore, Kim and Swartz (2001) *Biotechnol Bioeng.* 74:309-316; Kim and Swartz (1999) *Biotechnol Bioeng.* 66:180-188 have illustrated that the length of the conventional batch reaction could be extended from 20 minutes to up to 2 hours with the use of novel energy regeneration systems. While these approaches are promising, there is still a tremendous need for developing an economically viable commercial process. Increasing the product yield by improving the protein production rate and extending the reaction time is an essential component of filling this need. Reducing the cost of protein synthesis reagent, especially the chemical energy source, is another important component.

Relevant Literature

U.S. Pat. No. 6,337,191 B1, Swartz et al. Kim and Swartz (2000) *Biotechnol Prog.* 16:385-390; Kim and Swartz (2000) *Biotechnol Lett.* 22:1537-1542; Kim and Choi (2000) *J Biotechnol.* 84:27-32; Kim et al. (1996) *Eur J Biochem.* 239: 881-886.

SUMMARY OF THE INVENTION

Compositions and methods are provided for the enhanced in vitro synthesis of biological molecules. Of particular interest is the synthesis of polymers, e.g. nucleic acids, polypeptides, and complex carbohydrates. The optimized conditions for synthesis permit the in vitro activation of oxidative phosphorylation in the reaction mixture, which provides for enhanced yield of the product of synthesis. The conditions also provide for enhanced yield of biologically active polypeptides, by improving the conditions for folding. The activation of oxidative phosphorylation may be evidenced by the ability of the reaction mixture to generate synthesis of a polymer in the absence of currently utilized secondary energy sources or glycolytic intermediates. The activation of oxidative phosphorylation can also be demonstrated by the sensitivity of the reaction mixture to specific inhibitors of this pathway.

DETAILED DESCRIPTION OF THE EMBODIMENTS

Figure 1:
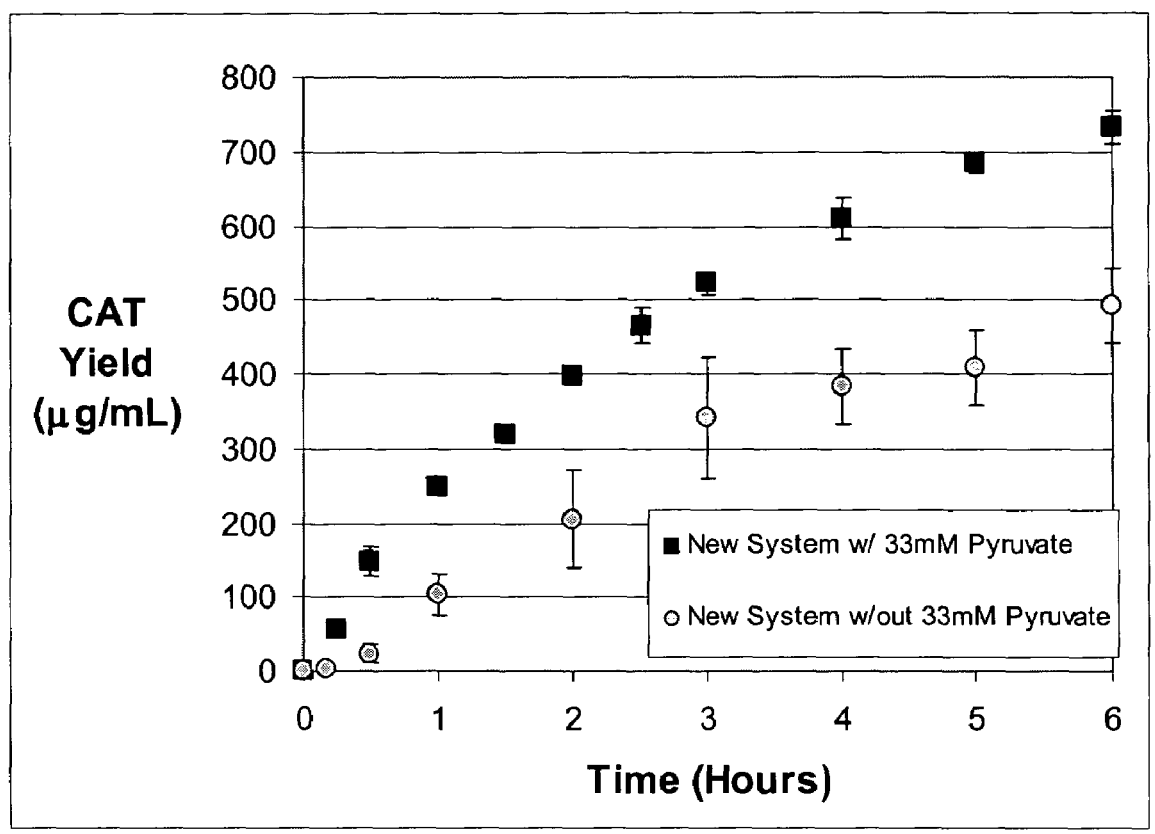
FIG. 1 is a graph depicting in vitro protein synthesis with the component system of the present invention, in the absence and presence of added pyruvate. Even in the absence of added pyruvate, significant protein synthesis occurs.

Compositions and methods are provided for the enhanced in vitro synthesis of biological molecules, in which oxidative phosphorylation is activated, providing for increased yields and enhanced utilization of energy sources. The system is referred to herein as the Cytomim system. Improved yield is obtained by a combination of reaction conditions, which conditions may include, without limitation, the use of biological extracts derived from bacteria grown on a glucose containing medium; an absence of polyethylene glycol; and optimized magnesium concentration.

Cell-free protein synthesis exploits the catalytic power of the cellular machinery. Obtaining maximum protein yields in vitro requires adequate substrate supply, e.g. nucleoside triphosphates and amino acids; a homeostatic environment; catalyst stability; and the removal or avoidance of inhibitory byproducts. The optimization of in vitro synthetic reactions benefits from recreating the in vivo state of a rapidly growing organism.

The methods and compositions of the present invention better reflect the cytoplasmic environment of a bacterial cell, and result in significant improvements in protein production and protein folding over the methods of the prior art. In addition, the pathway for oxidative phosphorylation has been activated. The reaction conditions that generate this more natural environment result from providing a combination of the factors, as described above. This system is capable of significant protein production for up to 6 hours in an in vitro batch reaction. Remarkably, the system does not require the addition of commonly used secondary energy sources, such as phosphoenolpyruvate, creatine phosphate, acetyl phosphate, glucose-6-phosphate, pyruvate or glycolytic intermediates. By mimicking the cellular environment, an enhanced synthetic capability is provided.

In preferred embodiments of the invention, a reaction mixture as described herein is used for synthesis, where the reaction provides for activation of oxidative phosphorylation. However, certain benefits of the invention, including enhanced synthesis of active polypeptides through improved conditions for protein folding, do not require activation of oxidative phosphorylation. Performing synthesis in the substantial absence of polyethylene glycol provides for improved folding; and may further be combined with, for example, the methods described in U.S. Pat. No. 6,548,276, herein incorporated by reference.

Folding, as used herein, refers to the three-dimensional structure of polypeptides and proteins or the process of attaining such a structure, where interactions between amino acid residues act to stabilize the structure. While non-covalent interactions are important in determining structure, usually the peptides and proteins of interest will have intra- and/or intermolecular covalent bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The Cytomim system is homeostatic with respect to phosphate concentrations and pH, the duration of protein synthesis is significantly prolonged, and biological synthesis can occur even in the absence of obvious secondary energy sources. One advantage of the methods is the ability to utilize inexpensive energy sources for synthesis. Another advantage is the ability to generate higher yields. In a comparable reaction, the Cytomim system can provide for improved yields of from about 2-fold higher; from about 3-fold higher; and may be from about 8-fold higher, or more, where the comparison is based on the PANOx system, as described by Kim and Swartz (2000), supra.

In vitro synthesis, as used herein, refers to the cell-free synthesis of biological macromolecules in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

The more natural environment for synthesis utilizes cell extracts derived from bacterial cells grown in medium containing glucose and phosphate, where the glucose is present at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as *E. coli*, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, N.Y. for examples of glucose containing media).

Another important change in the reaction mixture is the substantial absence of polyethylene glycol (PEG). A conventional reaction mixture (for example, see Kim and Swartz, 2001) contains about 2% polyethylene glycol 8000. However it is found that this diminishes the yield. In the present methods, the molecules spermidine and putrescine are used in the place of PEG. Spermine or spermidine is present at a concentration of at least about 0.5 mM, usually at least about 1 mM, preferably about 1.5 mM, and not more than about 2.5 mM. Putrescine is present at a concentration of at least about 0.5 mM, preferably at least about 1 mM, preferably about 1.5 mM, and not more than about 2.5 mM.

The concentration of magnesium in the reaction mixture affects the overall synthesis. Often there is magnesium present in the cell extracts, which may then be adjusted with additional magnesium to optimize the concentration. Sources of magnesium salts useful in such methods are known in the art. In one embodiment of the invention, the source of magnesium is magnesium glutamate. A preferred concentration of magnesium is at least about 5 mM, usually at least about 10 mM, and preferably a least about 12 mM; and at a concentration of not more than about 20 mM, usually not more than about 15 mM. Other changes that may enhance synthesis include the removal of HEPES buffer and phosphoenol pyruvate from the reaction mixture.

The present system is the first to demonstrate the synthesis of proteins without a secondary energy source, such as PEP, creatine phosphate, and acetyl phosphate, or glycolytic intermediate, such as glucose, glucose-6-phosphate, and pyruvate. Furthermore, it does not require the addition of exogenous enzymes. Pyruvate has been used to enhance protein synthesis, although it is not required, as noted in FIG. 1. By more effectively reproducing the cytoplasmic conditions and utilizing conditions that are more physiologically relevant, the new system maintains better homeostasis than conventionally used cell-free systems. The present system does not accumulate phosphate, which is known to inhibit protein synthesis. Conventional secondary energy sources result in phosphate accumulation. In addition to avoiding the accumulation of an inhibitor of protein synthesis, the present system is capable of maintaining a stable pH over the course of the reaction.

As previously stated, the compositions and methods of this invention allow for production of proteins without a secondary energy source; however, a secondary energy source may be added to supplement synthesis. In particular, glycolytic intermediates, such as glucose, glucose-6-phosphate, fructose-6-phosphate, fructose-1,6-diphosphate, triose phosphate, 3-phosphoglycerate, 2-phosphoglycerate, phosphoenolpyruvate (PEP), and pyruvate may be used.

Other compounds useful as an energy source are compounds that generate reduction equivalents, or activate a pathway that generates reduction equivalents. Such compounds include amino acids, e.g. glutamate, compounds in the tricarboxylic acid (TCA) cycle, citrate, cis-aconitate, isocitrate, α-ketoglutarate, succinyl-CoA, succinate, fumarate, malate, oxaloacetate, and glyoxylate, or compounds that can be directed into central metabolism (glycolysis and the TCA cycle). It is preferable that secondary energy sources, if added, are homeostatic with respect to phosphate accumulation, such as glucose or glutamate. The energy source may be supplied in concentrations of at least about 10 mM, of at least about 20 mM, more usually at least about 30 mM. Such compounds are not usually added in concentrations greater than about 250 mM, more usually not greater than about 150 mM. Additional amounts of the energy source may be added to the reaction mixture during the course of protein expression, in order to extend reaction times.

The system can be run under aerobic and anaerobic conditions. Oxygen may be supplied, particularly for reactions larger than 15 µl, in order to increase synthesis yields. The headspace of the reaction chamber can be filled with oxygen; oxygen may be infused into the reaction mixture; etc. Oxygen can be supplied continuously or the headspace of the reaction chamber can be refilled during the course of protein expression for longer reaction times. Other electron acceptors, such as nitrate, sulfate, or fumarate may also be supplied in conjunction with preparing cell extracts so that the required enzymes are active in the cell extract.

It is not necessary to add exogenous cofactors for activation of oxidative phosphorylation. Compounds such as nicotinamide adenine dinucleotide (NADH), NAD$^+$, or acetyl-coenzyme A may be used to supplement protein synthesis yields but are not required. Addition of oxalic acid, a metabolic inhibitor of phosphoenolpyruvate synthetase (Pps), may be beneficial in increasing protein yields, but is not necessary.

The template for cell-free protein synthesis can be either mRNA or DNA. Translation of stabilized mRNA or coupled transcription and translation converts stored information into protein. The coupled system, generally utilized in *E. coli* systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally present at a concentration of at least about 50 mM, and not more than about 250 mM. Ammonium may be present, usually at a concentration of not more than 200 mM, more usually at a concentration of not more than about 100 mM. Usually, the reaction is maintained in the range of about pH 5-10 and a temperature of about 20°-50° C.; more usually, in the range of about pH 6-9 and a temperature of about 25°-40° C. These ranges may be extended for specific conditions of interest.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Vesicles, either purified from the host organism (see Muller and Blobel (1984) "In vitro translocation of bacterial proteins across the plasma membrane of *Escherichia coli*", PNAS 81:7421-7425) or synthetic, may also be added to the system. These may be used to enhance protein synthesis and folding. The technology described herein has been shown to activate the oxidative phosphorylation process that utilizes cytoplasmic membrane components. Inverted membrane vesicles containing respiratory chain components and the $F_1F_0$ATPase must be present for the activation of oxidative phosphorylation. The present methods also may be used for cell-free reactions to activate other sets of membrane proteins; for example, to insert or translocate proteins or to translocate other compounds.

Methods for Enhanced In Vitro Synthesis

Synthetic systems of interest include systems for the replication of biopolymers, which can include amplification of DNA, transcription of RNA from DNA or RNA templates, translation of RNA into polypeptides, and the synthesis of complex carbohydrates from simple sugars. Enhanced synthesis may include increases in the total or relative amount of polypeptide synthesized in the system; increases in the total or relative amount of polypeptide synthesized per unit of time; increases in the total or relative amount of biologically active polypeptide synthesized in the system; increases in the total or relative amount of soluble polypeptide synthesized in the system, and the like.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

The reactions may be of any volume, either in a small scale, usually at least about 1 µl and not more than about 15 µl, or in a scaled up reaction, where the reaction volume is at least about 15 µl, usually at least about 50 µl, more usually at least about 100 µl, and may be 500 µl, 1000 µl, or greater. In most cases, individual reactions will not be more than about 10 ml, although multiple reactions can be run in parallel. However, in principle, reactions may be conducted at any scale as long as sufficient oxygen (or other electron acceptor) is supplied.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors, initiation factors, and ribosome recycling factors. Cell-free systems known in the art include *E. coli* extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salt, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. of acetic acid or sulfuric acid). One or more of such salts may have amino acids as a counter anion. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time. The adjuster of oxidation/reductionpotential may be dithiothreitol, ascorbic acid, glutathione and/or their oxidized forms. Also, a non-denaturing surfactant such as Triton X-100 is optionally included, at a concentration of not more than about 500 mM, more usually not more than about 250 mM.

When using a protein isolating means in a continuous operation mode, the product output from the reactor flows through a membrane and into the protein isolating means. In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules immobilized with a component for adsorbing the synthesized, desired protein, and a membrane with pores of proper sizes. Preferably, the protein isolating means comprises two columns for alternating use.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

A standard reaction mixture for a coupled transcription-translation reaction, herein referred to as the PANOx system (Kim and Swartz (2001), supra.) contains the following components: 57 mM HEPES-KOH (pH7.5), 1.2 mM ATP, 0.85 mM each of GTP, UTP and CTP, 1 mM DTT, 200 mM potassium glutamate, 80 mM ammonium acetate, 16 mM magnesium acetate, 34 µg/ml folinic acid, 170.6 µg/ml $E.$ $coli$ tRNA mixture, 13.3 µg/ml plasmid, 100 µg/ml T7 RNA polymerase, 2 mM each of 20 unlabeled amino acids, 11 µM [$^{14}$C]leucine, 2% Poly(ethylene glycol) 8000, 33 mM PEP, 0.33 mM nicotinamide adenine dinucleotide, 0.26 mM Coenzyme A, 2.7 mM sodium oxalate and 0.24 volumes of S30 extract. Prokaryotic cell-free protein synthesis is performed using a crude S30 extract derived from $Escherichia$ $coli$ K12 (strain A19 ΔtonA ΔtnaA ΔspeA ΔendA met+), with slight modifications from the protocol of Pratt, J. M. 1984. (Coupled transcription-translation in prokaryotic cell-free systems. In Transciption and translation: a practical approach. Hanes, B. D., and S. J. Higgins. (Eds.). p. 179-209. IRL Press, New York.) T7 RNA polymerase was prepared from $E.$ $coli$ strain BL21 (pAR1219) according to the procedures of Davanloo et al. 1984. (Cloning and expression of the gene for bacteriophage T7 RNA polymerase. Proc Natl Acad Sci USA 81:2035-2039.)

The Cytomim environment for synthesis, according to the methods of the present invention, is as follows: cells for the extract are grown with 2YTPG media (Kim and Choi) containing glucose and phosphate. With reference to the PANOx system described above, HEPES buffer is removed, potassium glutamate concentration is reduced to 130 mM, 10 mM ammonium glutamate is used instead of 80 mM ammonium acetate, 8 mM magnesium glutamate is used instead of 16 mM magnesium acetate, 2% poly(ethylene glycol) 8000 is replaced with 1.5 mM spermidine and 1 mM putrescine, T7 RNA polymerase concentration is increased to 100 µg/ml, plasmid concentration is increased to 13.3 µg/ml, and phosphoenolpyruvate is removed from the reaction. The system can be enhanced with the addition of 33 mM sodium pyruvate, although this is not necessary. There was approximately an additional 3.3 mM magnesium, 14.4 mM potassium, 2.4 mM TRIS, and 23.5 mM acetate in each reaction originating from the cell extract.

Reactions were incubated at 37° C. for 5-6 hours. The amount of synthesized protein is estimated from the measured TCA-insoluble radioactivities using a liquid scintillation counter (Beckman LS3801). (Kim et al. 1996). Soluble protein yields were determined as previously described. (Kim and Swartz 2000).

FIG. 1 shows the protein production of chloramphenicol acetyl transferase (CAT) with the compositions and methods embodied in this invention. The error bars represent the standard deviation for 4 separate experiments. The new reaction mixture, as specified above, was supplemented with 33 mM sodium pyruvate, squares, or not, circles.

Figure 2:
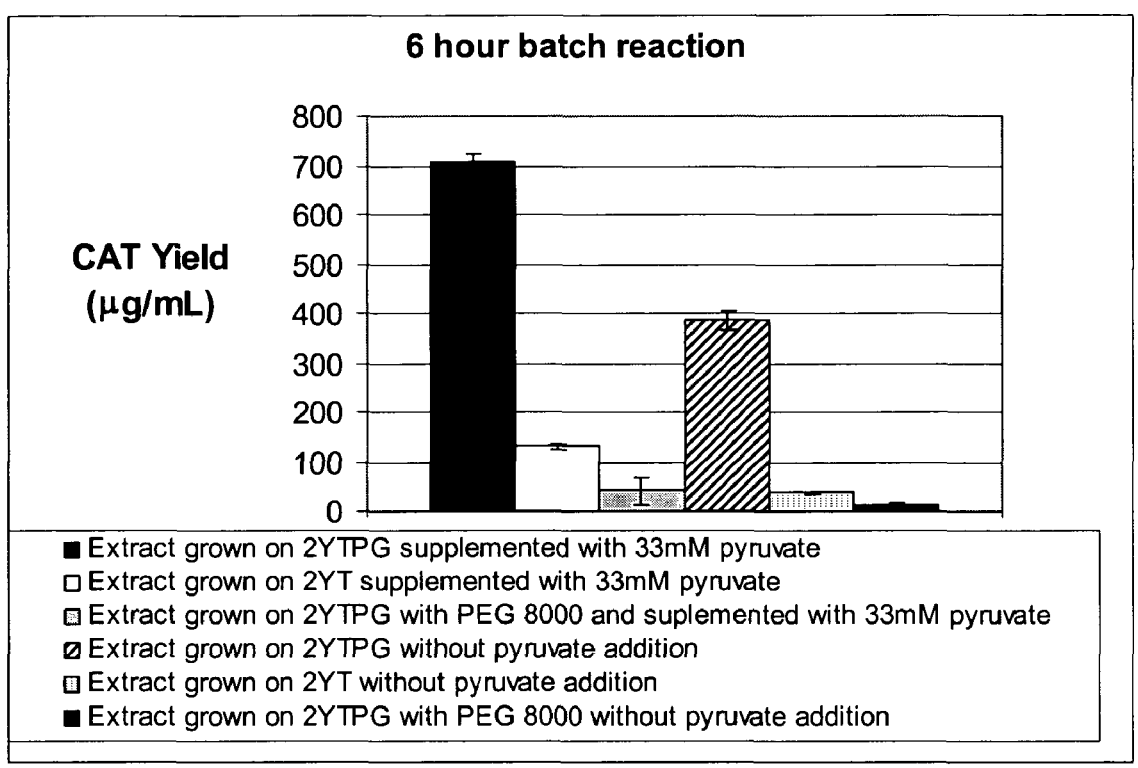
FIG. 2 is a bar graph depicting the level of protein synthesis, comparing extracts from bacteria grown under different conditions. It can be seen that cell extract produced from bacteria grown in a glucose containing medium provides for significantly better results, as does the absence of PEG in the reaction mixture.

FIG. 2 indicates that a combination of changes to the PANOx system is required for the creation of this new synthetic entity. In these data the magnesium concentration is in the preferred range, at approximately 11.3 mM. Unless indicated in the figure that the reaction contains polyethylene glycol (PEG) 8000, reactions contain 1.5 mM spermidine and 1 mM putrescine and use the reaction mixture described above for the new system. The data is given in two sets of three. The first three results are enhanced by 33 mM sodium pyruvate. The second set of data is without the addition of sodium pyruvate. In both data sets, extract that has been grown on 2YTPG produces significantly more protein than extract grown on 2YT. Moreover, this data shows that the removal of PEG 8000 is necessary for the increased yields provided by this new invention.

Figure 3:
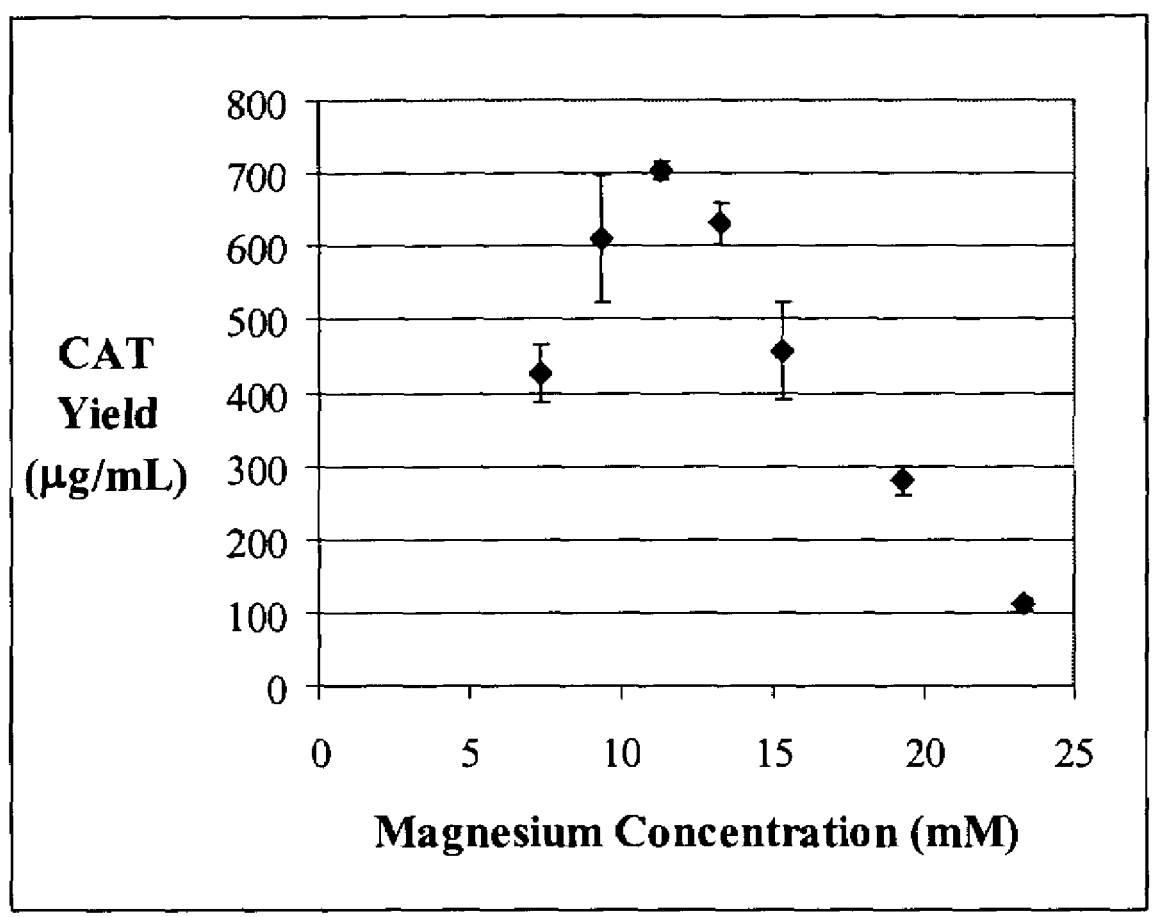
FIG. 3. Magnesium dependence of the system. 15 μl reactions were incubated for 6 hours with increasing amounts of Mg. The concentration of Mg shown includes the Mg present in the cellular extract. CAT expression was determined from $^{14}C$-leucine incorporation. Error bars represent the standard deviation from three to eight separate experiments.

FIG. 3 shows the magnesium concentration dependence associated with the new environment for protein expression. The optimum concentration is approximately 11 mM. The compositions for the reaction mixture are as described above for the present system. In all cases, synthesis is enhanced by 33 mM sodium pyruvate. A similar profile has been measured for the new environment without pyruvate. The magnesium concentration has been reduced more than 2-fold from the standard reaction mixture. When magnesium glutamate is used in the standard reaction mixture, its optimal value is 23.3 mM and with magnesium acetate, it is 19.3 mM. Reducing the magnesium concentration is the third requirement for the new environment.

In addition to the solutes that are added to the cell-free reaction mixture, salts can also be incorporated into the reaction by dialysis into the extract. Specifically, in the traditional method for cell extract preparation, the last step is repeated dialysis to bring the final ionic composition in the extract to 10 mM tris-(hydroxymethyl)aminomethane (TRIS, pH 8.2 with glacial acetic acid), 60 mM potassium acetate, and 14 mM magnesium acetate. This procedure was used for the experiments described. Therefore, in the absence of exogenous salts, the reaction has a starting concentration of approximately 3.3 mM magnesium, 14.4 mM potassium, 2.4 mM TRIS, and 23.5 mM acetate, originating from the cell extract. All of the reported concentrations include the contribution for the cell extract components.

Figure 4:
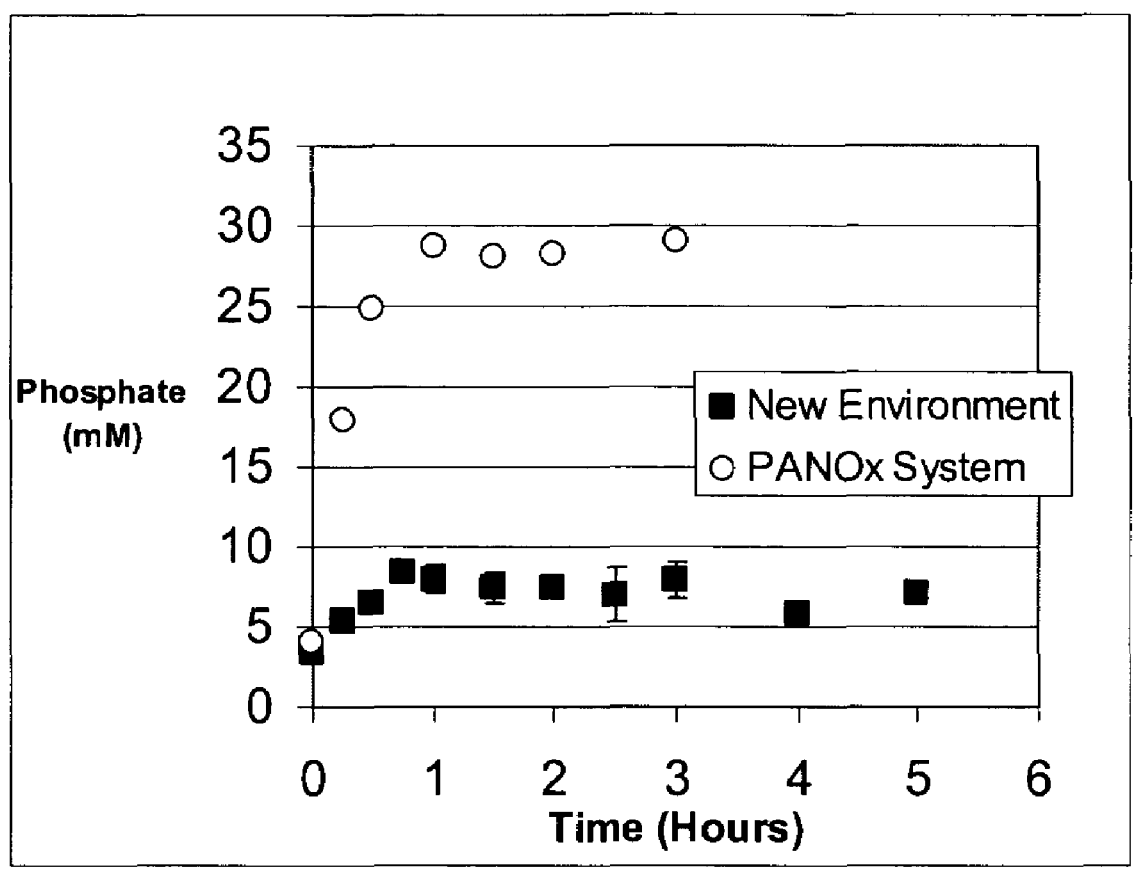
FIG. 4 is a graph comparing the phosphate levels in in vitro synthesis reactions.
Figure 5:
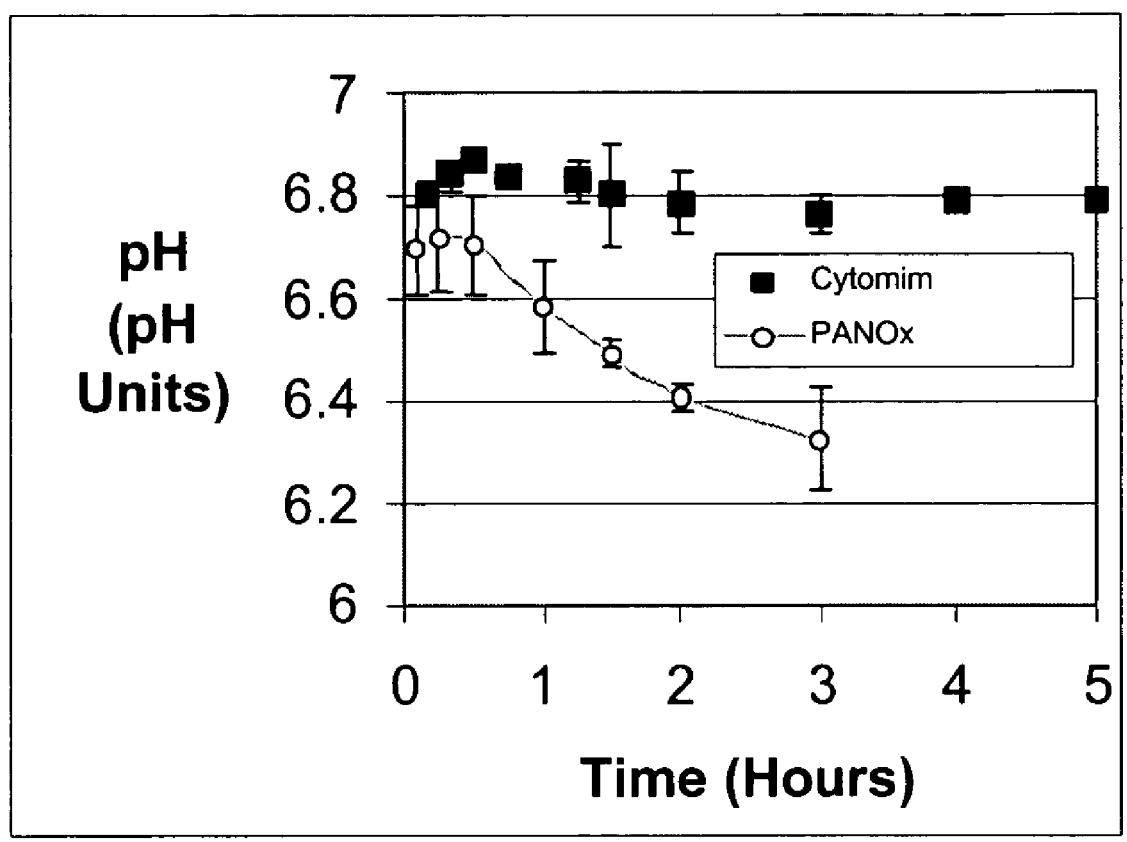
FIG. 5 is a graph illustrating the ability of the present methods to maintain pH levels.

The other components of the reaction mixture were optimized through various ranges of concentrations in order to create an overall balance of the reagents within this new entity for protein expression. The result is a new reaction composition that extends the duration of protein synthesis for up to six hours (FIG. 1) and that stabilizes the phosphate concentration (FIG. 4) and the reaction pH (FIG. 5) during the course of the synthesis reaction. These stabilized conditions may contribute to improved protein folding, as well as enhanced synthesis.

This new system has also demonstrated the first evidence of activating oxidative phosphorylation within the cell-free system. Oxidative phosphorylation produces energy by coupling the transfer of electrons to oxygen, a final electron acceptor, for the generation of ATP. This process is utilized to efficiently provide energy for cells growing aerobically.

Capturing this process via this invention is substantially advantageous to the cell-free system, since it offers a very effective method of regenerating energy in vitro. Activation of this energy generation pathway was discovered after realizing that the actual yield, based on energy requirements for protein production was approximately 175% of the maximum theoretical yield expected using pyruvate as the anaerobic energy source. For reference, the ATP efficiency for the PANOx and conventional PEP systems are approximately 50% and 20% of the theoretical maximum, respectively.

Figure 6:
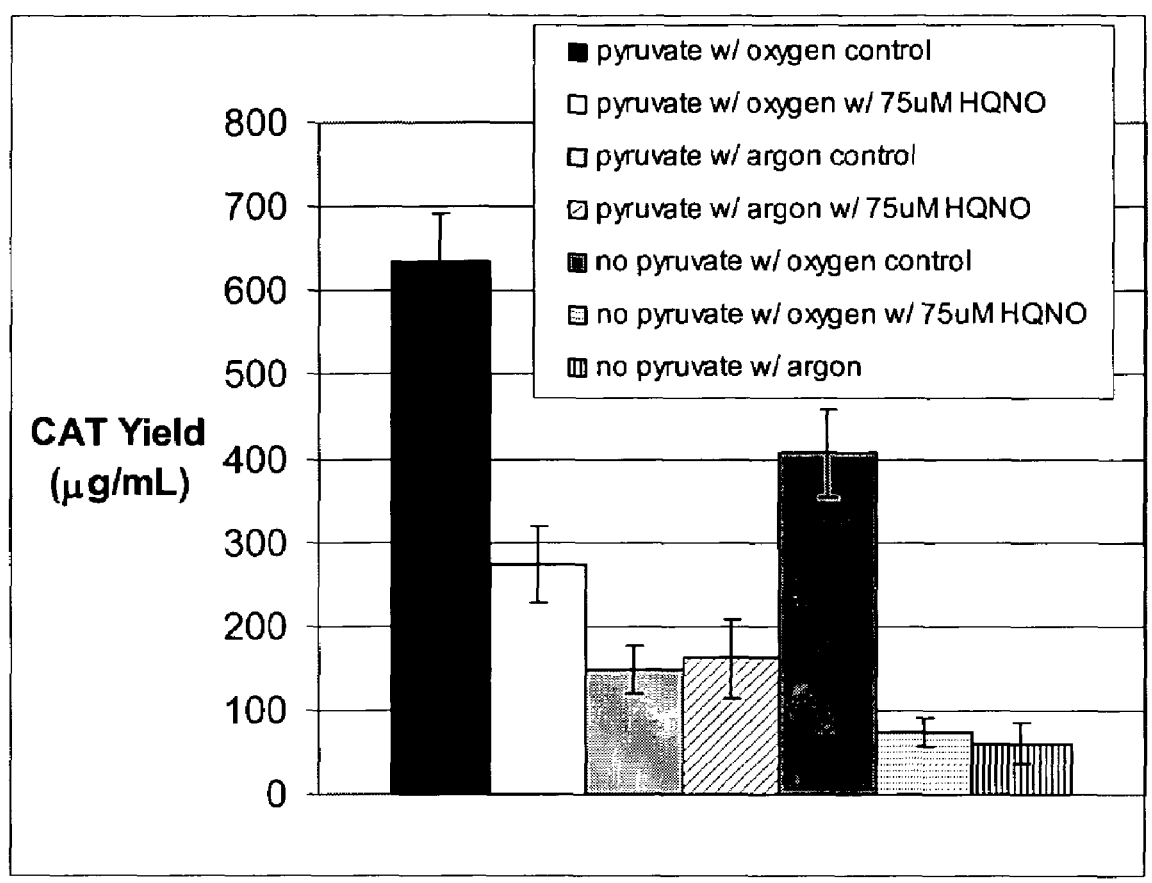
FIG. 6 is a bar graph depicting the effect of oxygen and HQNO, an inhibitor of oxidative phosphorylation, on in vitro synthesis using the present invention.

In seeking to understand how this yield was accomplished, inhibitors of oxidative phosphorylation were tested to establish that this process was partially responsible for the protein production capability of this new technology. FIG. 6 shows protein synthesis results of CAT using the new system under three separate conditions, with or without 2-heptyl-4-hydroxyquinoline-N-oxide (HQNO). HQNO inhibits the electron transport chain part of oxidative phosphorylation. All cases are 20 μl batch reactions, and were incubated at 37° C. for 5 hours. The head spaces of the batch reactors were filled with either oxygen or argon, an inert gas. If oxidative phosphorylation is active, one would expect that the protein synthesis yield should decrease upon the addition of the inhibitor of oxidative phosphorylation, HQNO, in the cases where oxygen is present. Furthermore, protein synthesis should be unaffected upon the addition of HQNO in the cases where argon is present and oxygen is not available.

The data in FIG. 6 support the conclusion that oxidative phosphorylation has been activated by the new environment. In the presence of oxygen, synthesis using the new system, with or without pyruvate, substantially decreases after HQNO addition and is unaffected by HQNO in the argon cases. Similar studies have been carried out with the following inhibitors of oxidative phosphorylation: 2,4-dinitrophenol, cyanide, azide, thenoyltrifluoroacetone, and carbonyl-cyanide-m-chlorophenylhydrazone. In all cases, the results support our conclusion that the new system has activated oxidative phosphorylation. It is important to note that protein synthesis yields in the PANOx system are unaffected by these same inhibitors.

Example 2

Effect of a Larger Scale Reaction Volume

Protein synthesis, using the methods of the invention, was performed at a 5 ml scale for synthesis of chloramphenicol acetyl transferase (CAT). Reactions were carried out at 37° C. in a 10 ml stirred glass beaker. CAT expression was determined from $^{14}$C-leucine incorporation. A small piece of stainless steel wire was threaded through a 30 cm long piece of silicone tubing. About 15 centimeters of the tubing (1.47 mm ID, 1.96 mm OD) was immersed in the cell-free reaction mixture by coiling inside the reactor. This tubing was pressurized with pure $O_2$ to deliver the oxygen necessary for the regeneration of ATP within the cell-free protein synthesis reaction. The consumed/degraded substrates were added in the following concentrations: 0.5 mM CTP, 0.5 mM UTP, 1.8 mM potassium hydroxide, 0.5 mM asparagine, 0.5 mM glutamine, 2 mM cysteine, 1 mM serine, 10 mM potassium glutamate, 0.05 mg/mL T7 RNA polymerase, and 0.007 mg/mL pK7CAT plasmid. The amino acid mixture contained asparagine, glutamine, threonine, cysteine, serine, and glutamate. It was added every thirty minutes in the fed reaction. UTP, CTP, potassium hydroxide, T7 RNA Polymerase and an additional 30 mM potassium glutamate were added at 1.2, 2.7, 4.2, and 6 hours. pK7CAT was added at 1.2 and 6 hours. 33 mM pyruvate was added at 2.7 hours. The error bars represent the high and low of two separate experiments. The total yield of CAT expressed was monitored by $^{14}$C-leucine incorporation. The soluble yield of CAT expressed was monitored by $^{14}$C-leucine incorporation. The active yield of CAT was determined by enzymatic assay according to the protocol of Shaw (1975) Meth Enzymol 43:737-755 (see also co-pending patent application 60/488,264)

Figure 7:
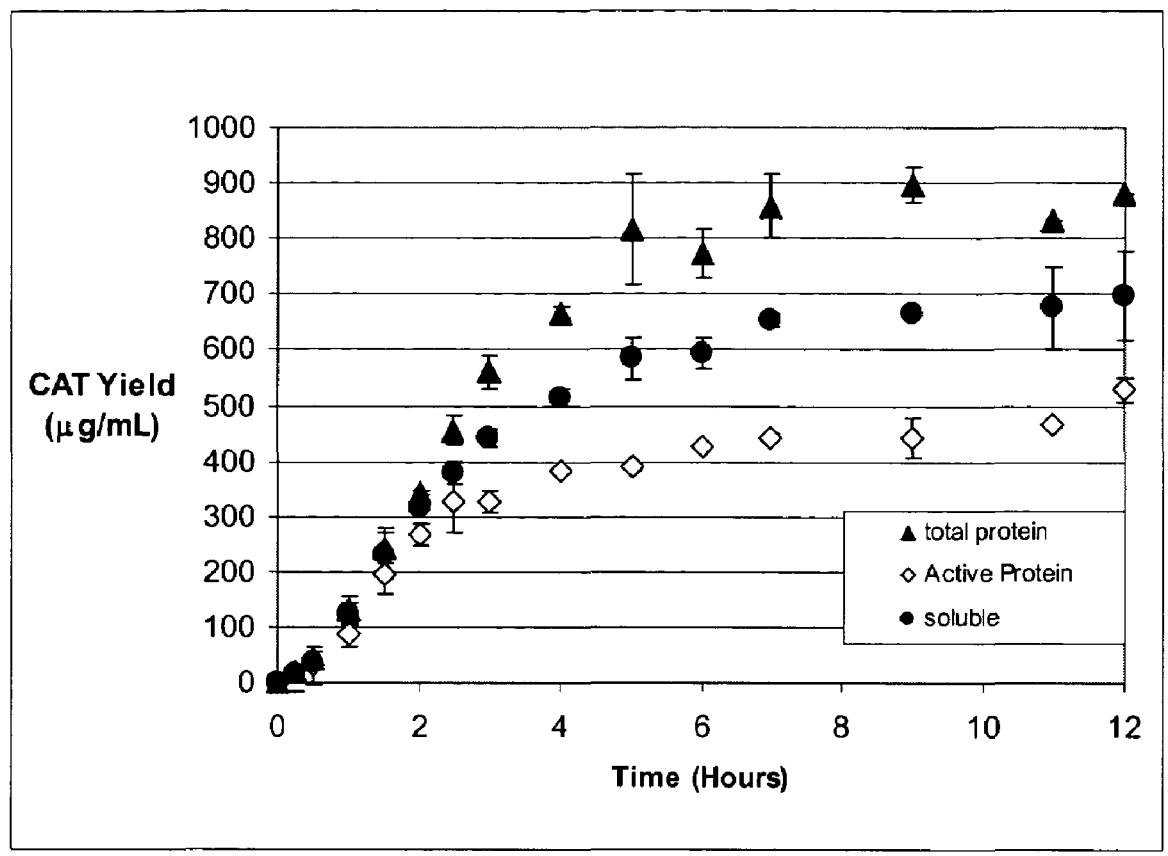
FIG. 7. 5 ml scale fed-batch experiments with the new in vitro protein synthesis system.

The data are shown in FIG. 7. This graph demonstrates the synthesis of approximately 100 nanomoles of active protein in a single reaction with the methods of the invention used in fed-batch operation. These methods are therefore shown to be useful for the convenient and economical production of large quantities of protein, e.g. in amounts sufficient for NMR structure analysis, for preclinical and clinical testing, and the like.

Example 3

Effect of Cofactors

Protein synthesis reactions were set up as described in Example 1 for the Cytomim system. 15 μl reactions were performed for 6 hours, expressing CAT. The error represents the standard deviation from 4 separate experiments. An "x" indicates the presence of that component. Protein production is given relative to a control with NAD and CoA. The control reactions (with NAD and CoA) produced 727 μg CAT/ml.

The concentration of cofactors CoA and NAD were varied as set forth in Table 2. As evidenced by the relative protein production, the removal of CoA had no significant effect. The removal of NAD reduces synthesis by about 10%.

TABLE 2

| Expressed Protein | 0.33 mM NAD | 0.26 mM CoA | Relative Protein Production |
|---|---|---|---|
| CAT | x | x | 1 ✤ 0.03 |
| CAT |   | x | 0.91 ✤ 0.05 |
| CAT | x |   | 1.02 ✤ 0.1 |
| CAT |   |   | 0.86 ✤ 0.03 |

Example 4

Synthesis of Tissue Plasminogen Activator

Elucidating the appropriate conditions for the correct folding of complex proteins is a central problem in cell-free expression. Although in vitro systems have been successful in efficiently folding several specific model proteins that require no or few disulfide bonds, such as CAT, achieving the proper folding of complex proteins has been challenging. This invention provides an environment that is better suited for producing complex proteins in their properly folded, active state. Tissue plasminogen activator (tPA) is a complex mammalian protein. The active domain of this protein, called v-tPA, contains the protease domain and one krinkle domain. v-tPA contains 9 disulfide bonds.

Reactions for the synthesis of v-tPA were set up in both the PANOx and Cytomim systems as described in example 1. Since vtPA requires an oxidizing environment, the cell extract was first treated with 1 mM iodoacetamide (IAM) and incubated at room temperature for 30 minutes before being added to the cell-free reaction mixture. Additionally these reactions included 75 µg/ml DsbC, 4 mM oxidized glutathione (GSSG) and 1 mM reduced glutathione (GSH). IAM treatment was first described by Swartz and Kim, U.S. Pat. No. 6,548,276.

The activity assay protocol for vtPA follows. Activity assays were run directly following a 3 hour PANOx reaction or a 6 hour reaction with the new environment. After centrifuging samples at 4° C., 15000 RCF for 15 minutes, 10 µl of supernatant was taken and added to a well in a microplate. Afterwards, 100 µl of assay reagent mixture buffer (9 parts Tris buffer and 1 part Chromozym t-PA solution; Tris buffer: 100 mM pH 8.5 Tris-CI buffer and 0.15% (w/v) Tween 80; Chromazym t-PA solution: 4 mM Chromazym t-PA in redistilled water, Roche Molecular Biochemicals, Indianapolis, Ind.) as added and mixed with the sample. The mixture was incubated at 37° C. for 10 minutes. The rate of change in absorbance at 405 nm was recorded in a microplate reader (SpectralMax 190, Molecular Devices, CA) by kinetics assay. The concentration of sample was calculated by comparison with a vtPA standard.

Even though approximately the same amount of total protein was produced by both the PANOx and the Cytomim systems, the amount of active v-tPA doubled using the new system when compared to the standard reaction mixture. (Table 1)

TABLE 1

|  | Total v-tPA (µg/mL) | Active v-tPA (µg/mL) |
| --- | --- | --- |
| Cytomim system | 232 | 44.8 |
| PANOx system | 211 | 22.7 |

Example 5

Spermidine and Putrescine Concentrations

Protein synthesis reactions were set up as described in Example 1 for the Cytomim system. 15 µl reactions were performed for 6 hours, expressing CAT. The concentrations of spermidine and putrescine were varied as set forth in Table 3. Spermidine was optimized with respect to protein production in the presence of 1 mM putrescine and putrescine in the presence of 1.5 mM spermidine.

TABLE 3

| Ionic Solute | Optimization profile (mM/fraction of maximum yield)* | | | | | |
| --- | --- | --- | --- | --- | --- | --- |
| New System | | | | | | |
| Spermidine | 0/0.53 | 0.5/0.90 | 1/0.97 | 1.5/1.00 | 5/0.48 | 10/0.15 |
| Putrescine | 0/0.95 | 1/1.00 | 3/0.80 | 7/0.58 | 11/0.43 | 15/0.23 |

*The values given as '1/0.97' indicate that a 1 mM concentration of that ionic solute was added to the reaction and that 97% of the maximum expression of CAT was achieved at that particular concentration. Only one solute was varied at a time. All other solutes were at the concentrations described in Example 1 for the new system.

Example 6

Comparison of Protein Synthesis

Figure 8:
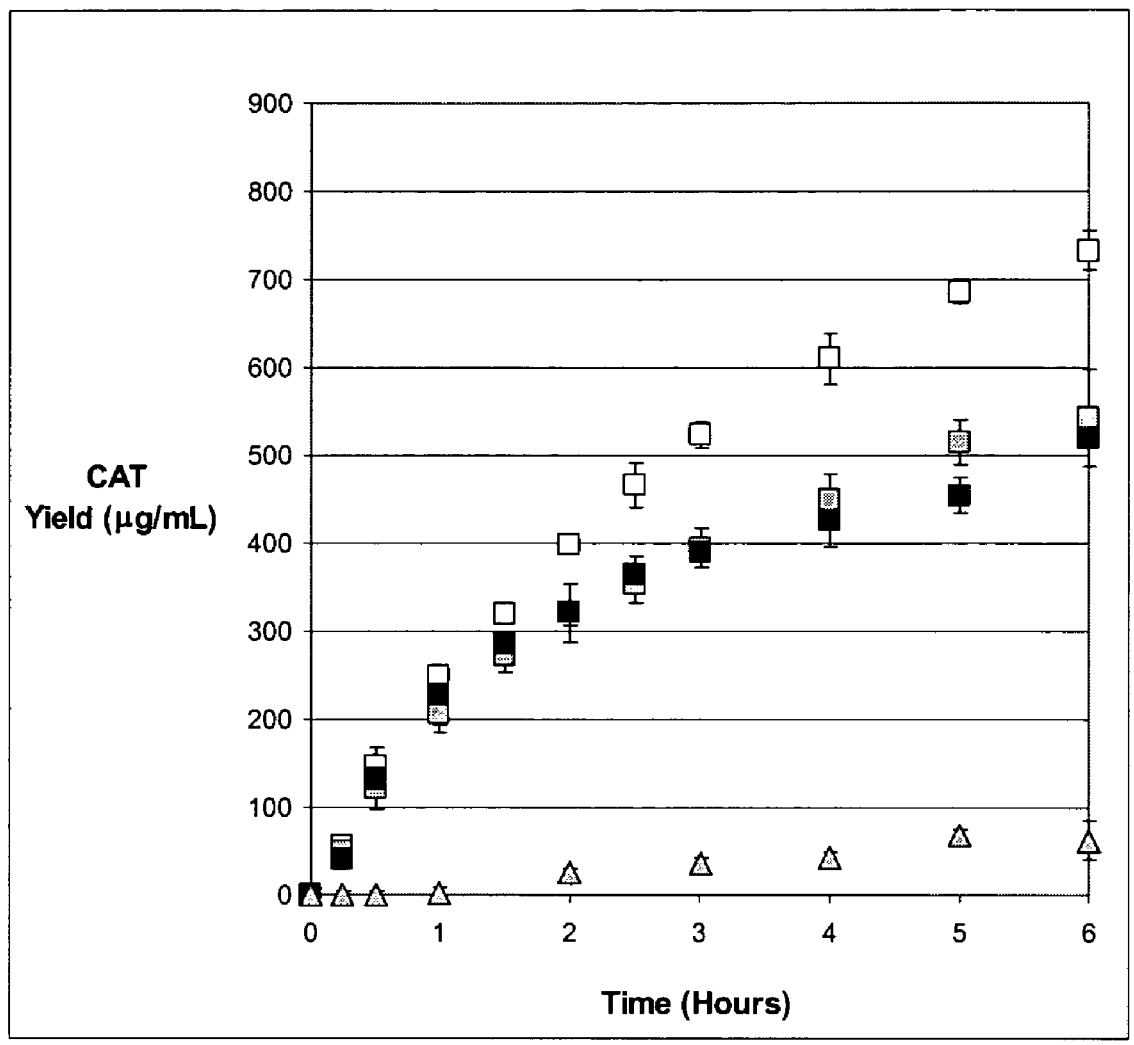
FIG. 8. Expression of CAT, comparing the PANOx system with pyruvate and the Cytomim system with pyruvate.

The amount of protein produced in the Cytomim environment is substantially improved compared to previous systems. As shown in FIG. 8, the Cytomim system produces higher total yield, as well as increased soluble and active protein yield.

Reactions were carried out for 6 hours and CAT expression was determined from $^{14}$C-leucine incorporation and enzymatic activity assay. 15 µl reaction mixtures were prepared in a different tube for each time point. At each time point, one tube was sacrificed in order to determine the amount of expressed protein. Error bars represent the standard deviation for three separate experiments for the PANOx system with pyruvate and six individual experiments for the Cytomim system. Squares: Cytomim system; Open, total yield of CAT expressed as monitored by $^{14}$C-leucine incorporation; Grey, soluble yield of CAT expressed as monitored by $^{14}$C-leucine incorporation; Closed, active yield of CAT as determined by enzymatic assay. Grey triangles, PANOx system using pyruvate as an energy source, total yield of CAT expressed as monitored by $^{14}$C-leucine incorporation.

In addition to the significant yields, this new technology offers an economical advantage over conventional cell-free systems. The high energy phosphate compounds that are conventionally used to regenerate ATP are generally the most expensive cost associated with cell-free expression. The Cytomim system can almost entirely eliminate this cost. Equivalent or higher protein yields at a fraction of the cost make the Cytomim system a very attractive method for cell-free protein synthesis.

What is claimed is:

1. A method for in vitro transcription of mRNA and/or translation of polypeptides, the method comprising:
    synthesizing said mRNA and/or polypeptides in a transcription and/or translation reaction mix substantially free of polyethylene glycol, comprising:
    an extract from *E. coli* cells comprising membrane vesicles containing respiratory chain components; components of polypeptide and/or mRNA synthesis machinery; a template for transcription of said mRNA and/or translation of said polypeptide; monomers for synthesis of said mRNA and/or polypeptides; and cofactors, enzymes and other reagents necessary for said transcription and/or translation;
    magnesium at a concentration of from about 5 mM to about 20 mM;
    wherein oxidative phosphorylation, which is sensitive to electron transport chain inhibitors, is activated in said reaction mix.

2. The method of claim 1, wherein transcription of mRNA and/or translation of polypeptides is at least two fold higher than synthesis in the absence of said oxidative phosphorylation.

3. The method according to claim 1, wherein transcription of mRNA and/or translation of polypeptides is at least three fold higher than synthesis in the absence of said oxidative phosphorylation.

4. The method of claim 1 wherein said transcription of mRNA and/or translation of polypeptides is performed as a batch reaction.

5. The method of claim 1, wherein said transcription of mRNA and/or translation of polypeptides is performed as a continuous reaction.

6. A method for in vitro transcription of mRNA and/or translation of polypeptides, the method comprising:
synthesizing said mRNA and/or polypeptides in a transcription and/or translation reaction mix substantially free of polyethylene glycol, comprising:
an extract from *E. coli* cells grown in glucose and phosphate containing medium comprising components of polypeptide and/or mRNA synthesis machinery; a template for transcription of said mRNA and/or translation of said polypeptide; monomers for synthesis of said mRNA and/or polypeptides; and co-factors, enzymes and other reagents necessary for said transcription and/or translation;
magnesium at a concentration of from about 5 mM to about 20 mM;
at least one of spermine or spermidine at a concentration of at least about 1 mM;
wherein oxidative phosphorylation, which is sensitive to electron transport chain inhibitors, is activated in said reaction mix.

7. The method of claim 6 wherein said synthesis is performed as a batch reaction.

8. The method of claim 6, wherein said synthesis of polypeptides is performed as a continuous reaction.

9. The method of claim 6, wherein transcription of mRNA and/or translation of polypeptides is at least two fold higher than synthesis in the absence of said oxidative phosphorylation.

10. The method according to claim 6, wherein transcription of mRNA and/or translation of polypeptides is at least three fold higher than synthesis in the absence of said oxidative phosphorylation.

* * * * *

UNITED STATES PATENT AND TRADEMARK OFFICE
CERTIFICATE OF CORRECTION

| | | |
|---|---|---|
| PATENT NO. | : 7,338,789 B2 | Page 1 of 1 |
| APPLICATION NO. | : 10/643683 | |
| DATED | : March 4, 2008 | |
| INVENTOR(S) | : Swartz et al. | |

It is certified that error appears in the above-identified patent and that said Letters Patent is hereby corrected as shown below:

Col. 1, line 3, insert:

-- FEDERALLY-SPONSORED RESEARCH OR DEVELOPMENT

This invention was made with Government support under contract GM060615 awarded by the National Institutes of Health. The Government has certain rights in this invention. --

Signed and Sealed this
Second Day of August, 2011

David J. Kappos
*Director of the United States Patent and Trademark Office*